(12) United States Patent
Sezgin et al.

(10) Patent No.: US 10,398,650 B2
(45) Date of Patent: Sep. 3, 2019

(54) DEVELOPMENT OF CURCUMIN AND PIPERINE LOADED DOUBLE-LAYERED BIOPOLYMER BASED NANO DELIVERY SYSTEMS BY USING ELECTROSPRAY / COATING METHOD

(71) Applicant: Veliddin Canfeza Sezgin, Istanbul (TR)

(72) Inventors: Veliddin Canfeza Sezgin, Istanbul (TR); Oguz Bayraktar, Izmir (TR)

(73) Assignee: Veliddin Canfeza Sezgin, Istanbul (TR)

( * ) Notice: Subject to any disclaimer, the term of this patent is extended or adjusted under 35 U.S.C. 154(b) by 0 days.

(21) Appl. No.: 15/554,658

(22) PCT Filed: Oct. 2, 2015

(86) PCT No.: PCT/TR2015/050123
§ 371 (c)(1),
(2) Date: Aug. 30, 2017

(87) PCT Pub. No.: WO2016/167732
PCT Pub. Date: Oct. 20, 2016

(65) Prior Publication Data
US 2018/0028447 A1  Feb. 1, 2018

(30) Foreign Application Priority Data

Apr. 17, 2015  (TR) ................. 2015 04764

(51) Int. Cl.
| | |
|---|---|
| *A61K 9/16* | (2006.01) |
| *A61K 36/9066* | (2006.01) |
| *A61K 9/51* | (2006.01) |
| *A61K 36/67* | (2006.01) |
| *A61K 31/121* | (2006.01) |
| *A61K 31/4525* | (2006.01) |
| *A23P 20/20* | (2016.01) |
| *A23L 33/105* | (2016.01) |
| *A61K 9/00* | (2006.01) |
| *A61K 9/50* | (2006.01) |
| *A61K 31/12* | (2006.01) |
| *B82Y 5/00* | (2011.01) |

(52) U.S. Cl.
CPC ............ *A61K 9/167* (2013.01); *A23L 33/105* (2016.08); *A23P 20/20* (2016.08); *A61K 9/0056* (2013.01); *A61K 9/1652* (2013.01); *A61K 9/1658* (2013.01); *A61K 9/5036* (2013.01); *A61K 9/5089* (2013.01); *A61K 9/5161* (2013.01); *A61K 9/5169* (2013.01); *A61K 9/5192* (2013.01); *A61K 31/12* (2013.01); *A61K 31/121* (2013.01); *A61K 31/4525* (2013.01); *A61K 36/67* (2013.01); *A61K 36/9066* (2013.01); *A23V 2002/00* (2013.01); *B82Y 5/00* (2013.01)

(58) Field of Classification Search
None
See application file for complete search history.

(56) References Cited

U.S. PATENT DOCUMENTS 8,257,740 B1  9/2012  Sung et al.

FOREIGN PATENT DOCUMENTS

| CN | 102961368 B | 4/2014 |
|---|---|---|
| WO | 2014022660 A1 | 2/2014 |
| WO | 2014197640 A1 | 12/2014 |

OTHER PUBLICATIONS

Gomez-Estaca et al (Formation of zein nanoparticles by electrohydrodynannic atomization: Effect of the main processing variables and suitability for encapsulating the food coloring and active ingredient curcumin. Food Hydrocolloids 28 (2012) 82-91) (Year: 2012).*

Tu et al (Preparation, characterisation and evaluation of curcumin with piperine-loaded cubosome nanoparticles, Journal of Microencapsulation, 31:6, 551-559 (2014)) (Year: 2014).*

Luo et al (Preparation and characterization of zein/chitosan complex for encapsulation of α-tocopherol, and its in vitro controlled release study. Colloids and Surfaces B: Biointerfaces. vol. 85, Issue 2, Jul. 1, 2011, pp. 145-152), (Year: 2011).*

Wang et al (Recent advances of chitosan nanoparticles as drug carriers. International Journal of Nanomedicine 2011:6 765-774 (2011)). (Year: 2011).*

International Search Report for corresponding International Application No. PCT/TR2015/050123.

Jieying Liu et al: "Recent Programs in Studying Curcumin and its Nano-preparations for Cancer Therapy", Current Pharmaceutical Design, Apr. 1, 2013, pp. 1974-1993, XP055235628.

* cited by examiner

*Primary Examiner* — Jake M Vu

(74) *Attorney, Agent, or Firm* — Egbert Law Offices, PLLC

(57) ABSTRACT

A double-layered particle having a core layer formed of zein protein, in which the active agent curcumin and/or its derivatives are encapsulated, and an outer shell layer formed of chitosan and/or its derivatives, in which the active agent piperine is encapsulated, and which is coated over the core layer.

3 Claims, 7 Drawing Sheets

Figure 1:
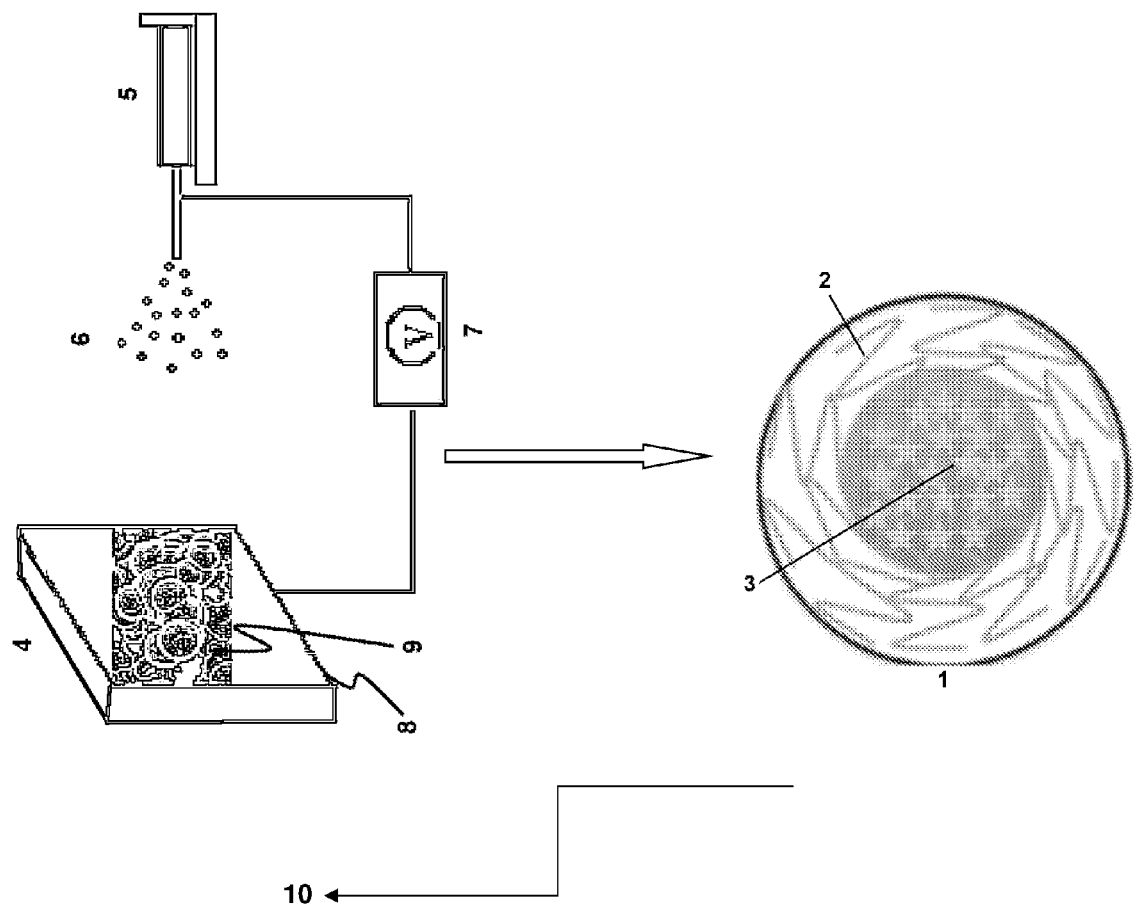

DEVELOPMENT OF CURCUMIN AND PIPERINE LOADED DOUBLE-LAYERED BIOPOLYMER BASED NANO DELIVERY SYSTEMS BY USING ELECTROSPRAY / COATING METHOD

THE RELATED ART

The invention relates to the preparation of multi-layered nano/micro particles with high added value comprising *curcuma* extract and piperine by using electrospray/coating method and to the application thereof to supplemental food nano-formulations.

The invention particularly relates to encapsulation of curcumin found to be effective on cancer and piperine known to improve bioavailability into double-layered nanoparticles produced by using the natural polymers zein and chitosan via electrospraying/coating method.

THE PRIOR ART

Curcumin is a compound obtained from the plant called *curcuma* (*Curcuma longa*). Curcumin having anti-tumoral characteristics besides its anti-oxidant, anti-microbial, and anti-inflammatory characteristics, is found to be effective in inhibiting development of various types of cancers such as leukemia, breast cancer, cervical, liver, mouth epithelium, ovarian, pancreas, and colon cancer etc.

Besides its effective and safe characteristics, one of the significant reasons why curcumin can not be used as a complete therapeutical agent is its low bioavailability. The reasons of having low bioavailability in oral application can be listed as: Low absorption, high metabolic rate, ineffective metabolic products, and high excretion rate from the body. However, other reasons reducing the bioavailability of curcumin include inability to be targeted to the cancerous tissue and ineffective drug distribution within the tissue.

In order to eliminate these drawbacks and make the best use of the potential therapeutical benefits of natural compounds, their application in encapsulated form within delivery systems are considered instead of direct application. Studies show that the activities of natural compounds are preserved significantly even after they are encapsulated (Kosaraju, 2008). Biopolymer based microspheres and drug-loaded liposomes are used in controlled release of drugs. In a study (1), emodins coated with silk fibroins comprising a biopolymer in their protein structure are found to be more effective on cancerous cells than uncoated ones.

In another study where curcumin is coated with silk fibroin and chitosan mixture; curcumin coated with silk fibroin is found to give better results than curcumin coated with silk fibroin-chitosan mixture in terms of cellular ingestion and loading. It is believed that mixing of chitosan with silk fibroin increases hydrophilic characteristic and the hydrophobic compound curcumin causes reduction in the efficiency of loading onto nanoparticles.

A method of increasing bioavailability in order to make the best use of potential therapeutical benefits is to apply natural compounds in encapsulated manner in delivery systems instead of their direct application and/or use bio-active natural compounds together with adjuvants increasing bio-availability.

Although the molecular mechanism of the black pepper active ingredient piperine, which is known to increase the bioavailability of curcumin, hasn't been clarified completely in the literature; it has been shown that it increases the period of release of drug in the body by means of reducing the activity of the enzymes playing a significant role in metabolization of CYP3A4 and p-glycoprotein etc. drugs. It is also shown that, piperine increases the absorption speed of drugs in the bowels by means of causing changes in the drug pharmacokinetics; and thus increases the speed of transfer into the blood by means of forming a structure especially together with the drugs having nonpolar chemical structures.

Piperine, being the primary component isolated from the black pepper plant (*Piper nigrum*), is the first recorded bioavailability improver scientifically accepted in 1979, and its bioavailability improving effect on drugs has been proven in various studies. The type of drugs, with which it has been used for improving bioavailability include a wide range of drugs from antituberculosis agents to cardiovascular and central nervous system drugs.

In a study made on healthy volunteers, it is found that, when piperine is used together with curcumin, it would increase the curcumin concentration in the serum and thus cause 154% improvement in bioavailability. Piperine is suggested to increase bioavailability in mechanisms such as connection to DNA receptors, regulation of cellular signal transmission, and inhabitation of drug flow pump. In general, piperine increases absorption by means of inhibiting the enzymes playing role in drug metabolism and the pumps enabling drug discharge from cells. In addition to these mechanisms, it can also increase absorption in the digestive system especially by inhibiting the enzymes playing role in drug metabolism in the liver.

In the prior art techniques, studies are found which include encapsulation of curcumin alone, encapsulation of piperine alone, or use of curcumin and piperine together.

The main reasons for application of encapsulating operation and the advantages of this operation are as follows: protection of sensitive substances such as plant extracts or chemical drugs from environmental conditions prior to use; better processability (solubility, viscosity, cellular ingestion); extending the expected life by means of preventing reactions such as oxidation and dehydration; and convenient use with the ability to provide controlled, continuous, and time release. Due to these advantages, encapsulated bioactive agents are commonly used in medicine, food, pharmaceutics, agriculture, cosmetics, and chemistry industries and are also supported by academic studies. Nowadays, plant extracts are preferred as active agents due to their antimicrobial, high phenol contents, and antioxidant properties.

Various studies are already present about encapsulation of polyphenols with microspheres using various biopolymers. In the literature, polyphenol encapsulation studies made with conventional methods since 2000 are reported and summarized (Fang & Bhandari, 2010). These methods include spray drying, coacervation, inclusion complex, and nanoemulsion etc. Said nanoparticle-based drug delivery systems can bring solution for compounds having low solubility in water such as curcumin. Nanoparticle drug delivery systems used in the delivery of hydrophilic and hydrophobic substances having high stability and delivery capacity can improve bioavailability by means of adjusting the circulation period, permeability, and release rate of compounds and providing resistance against metabolization.

During the research made in the literature, we have encountered some applications.

One of these applications is the patent application No. WO2011101859. In this application, nanoparticle comprising curcumin alone is obtained by means of using glycerol monooleate (GMO), polyvinyl alcohol (PVA), and pluronic F-127, and then emulsifying technique, and liophilization (freeze drying) technique. In this technique, it is not easy to keep the particle size distribution in a narrow range.

Another one is the patent application No. US2014065061. Said application comprises encapsulation of curcumin alone with liposomal-PLGA in liposome technique. One of its drawbacks is the inability of forming the particle size distribution in a narrow range; and another drawback is the low encapsulation efficiency.

Moreover, the activities of the bioactive compounds to be encapsulated may be reduced after being exposed to the conditions used in said encapsulation techniques.

Another patent is the Application No. WO2013171697. Said document comprises development of a formulation by using chitosan and polysorbate for oral administration route via dispersion of the active agent. Said application comprises a single-layered function.

Another similar article (2) belonging to C. Moorthi (January 2013) discloses that use of poloxamer and beta cyclodextrin (molecular encapsulation via inclusion complex method) with nano-sized curcumin would improve bioavailability, if used together with piperine or quercetin or silibinin. In said study, a double-layered function comprising a nanoparticle based drug delivery system is not found.

However, in a single-layered system, it is not possible to reach the efficiency of a double-layered system, which can make sequential release, or in other words, which can first perform the task of an enzyme inhibitor by means of rapidly releasing piperine, and then positively affects the efficiency by means of slow release of curcumin from the core part encapsulated by hydrophobic zein. Moreover, in the single-layered system, control of the release profiles (kinetics) is harder than the double-layered systems.

Another similar article (3) belongs to C. Moorthi (November 2012). In this article, a nanoparticle is found which comprises curcumin together with piperine. The methods used are: Thin film dehydration method, emulsion polymerization method, and Fess method. The drawbacks of these methods due to the chemicals and the conditions used are that: 1) They cause reduction of activity by means of interacting with the natural compound to be encapsulated; and 2) their application technique is hard. Similar to other applications and studies, said study also does not include a double-layered function comprising a nanoparticle based drug delivery system. Therefore, it is not easy to keep the particle size distribution in a narrow range and sequentially control the release profiles of active agents.

In the studies, bioavailability of curcumin was desired to be improved. However, studies for encapsulating both curcumin and piperine into nanoparticles with different polymer bases in the form of double-layered structure; couldn't be successful in terms of both drug targeting and visualization after cellular ingestion. The inadequacy of the prior art solutions has necessitated an improvement in the related technical field.

PURPOSE OF THE INVENTION

The present invention relates to the development of curcumin and piperine loaded double-layered biopolymer based nano delivery systems by using electrospray/coating method, which meets the above said requirements, eliminates all of the drawbacks and brings about some additional advantages.

The primary purpose of the invention is to encapsulate curcumin and/or its derivatives found to be effective against cancer and piperine that improves bioavailability into double-layered nanoparticles manufactured using natural polymers zein and chitosan/derivatives via electrospray/coating method and to improve the cellular ingestion efficiency of nanoparticles. In this way, the natural active agent curcumin can be delivered to a certain targeted tissue and it can reach the targeted site while maintaining its stability. By means of its piperine content, cellular ingestion of curcumin is made easier and thus its bioavailability and efficiency can be improved.

A purpose of the invention is to obtain a multi-layered nano/micro particle formed of a core part comprising *curcuma* extract with the active agent curcumin and/or its derivatives and a shell part comprising black pepper extract with the active agent piperine.

A similar purpose of the invention is to narrow down the particle size distribution range with regard to prior art techniques. At the same time, another purpose is to enable said double-layered delivery system first provide rapid release of piperine; and then provide controlled release of curcumin and/or its derivatives.

Another purpose of the invention is to encapsulate the *curcuma* extract comprising curcumin and/or its derivatives with zein that is known as maize protein via electrospray method in order to form the core part. In this way, *curcuma* extract is prevented from being affected by external factors and thus maintains its stability and provides controlled release of its active agent content. Moreover, coating of curcumin and/or its derivatives with zein improves bioavailability and these compounds are compatible with each other due to their hydrophobic nature.

Another purpose of the invention is to encapsulate the black pepper extract comprising the active agent piperine with chitosan and/or its derivatives via electrospray method in order to form the shell part.

Another purpose of the invention is to use the electrospray method as the encapsulation technique. Said electrospray method is more economic, practical, quicker, and more advantageous than the prior art methods by being bioavailable. Besides, during the encapsulation operation, no loss occurs in the bioactivity of the natural compound.

Another purpose of the invention is to ensure the stability of the extracts and provide the characteristics of the biomaterial via said electrospray method. In this way, usage potential is provided for practical food supplemental applications due to synergistic effects to be obtained with the use of the extracts together.

Another purpose of the invention is to provide better control of the particle size distribution and enable a narrower particle size distribution with said electrospray method.

A similar purpose of the invention is to use natural biopolymers zein and chitosan/derivatives in nanoparticle formation, and thus prevent formation of inflammation in interbody uses due to the bioavailability and low cytotoxic activity of these substances.

Another purpose of the invention is to form the shell part comprising black pepper extract with the active agent piperine on the core part comprising the *curcuma* extract via coating method. In this way, double-layered nano/micro particles are prepared.

A similar purpose of the invention is to obtain bioactive, bioavailable, stable, multi-functional particles that can be used in nanoformulations due to the encapsulated *curcuma* extract and piperine. Afterwards, the purpose is to use the prepared particles in food supplemental formulations with varying ratios by dispersion into solutions formed of plantal glycerine and water mixture.

In order to achieve the above said purposes, the invention comprises:

A double-layered particle (1) comprising:
- a. a core layer (3) formed of zein protein, in which the active agent curcumin and/or its derivatives are encapsulated, and
- b. an outer shell layer (2) formed of chitosan and/or its derivatives, in which the active agent piperine is encapsulated, and which is coated over said core layer (3).

The structural and characteristic features of the invention and all advantages will be understood better in detailed descriptions with the figures given below and with reference to the figures, and therefore, the assessment should be made taking into account the said figures and detailed explanations.

FIGURES FOR BETTER UNDERSTANDING OF THE INVENTION

FIG. 1: is the schematic view of the process of obtaining double-layered nano/micro particles comprising standardized *curcuma* and black pepper extracts via electrospray/coating method.

Figure 2A:
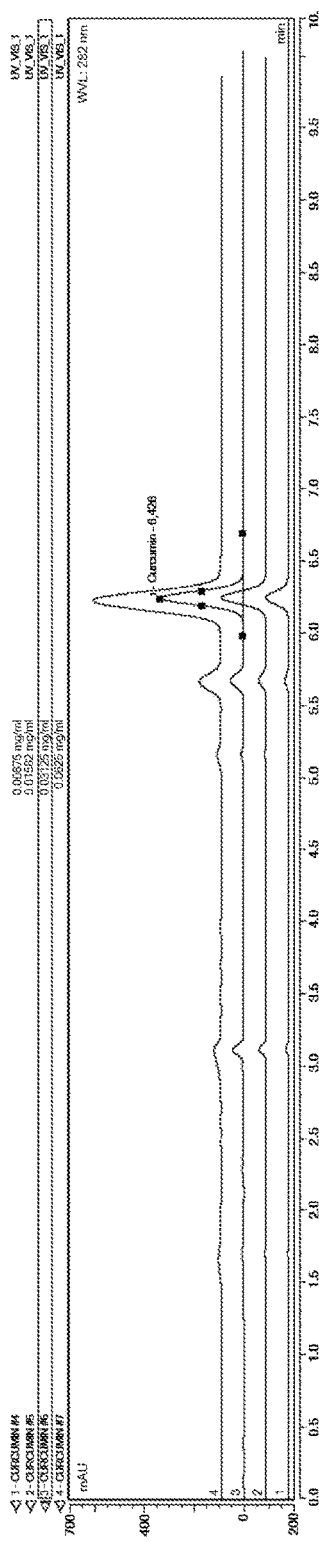

FIG. 2a: is the view of the peaks of standard curcumin solutions.

Figure 2B:
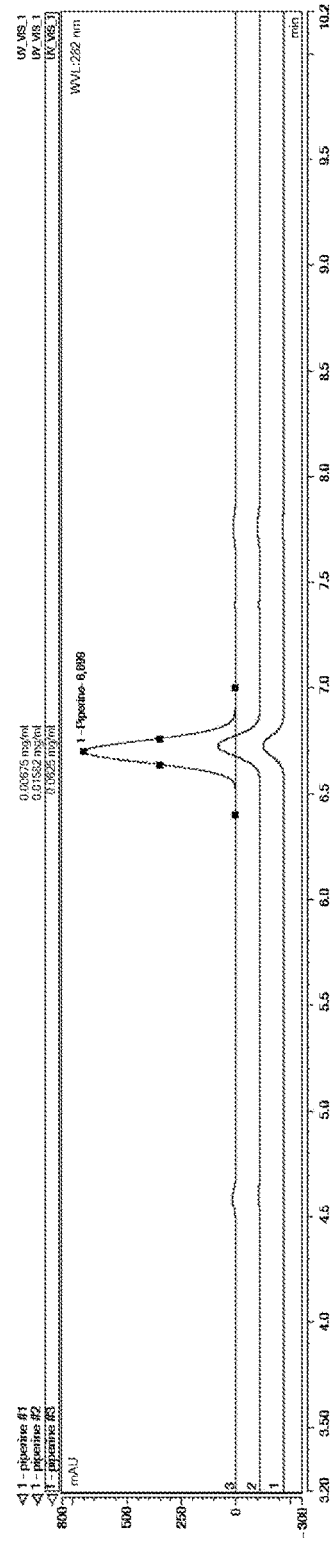

FIG. 2b: is the view of the peaks of standard piperine solutions.

Figure 3:
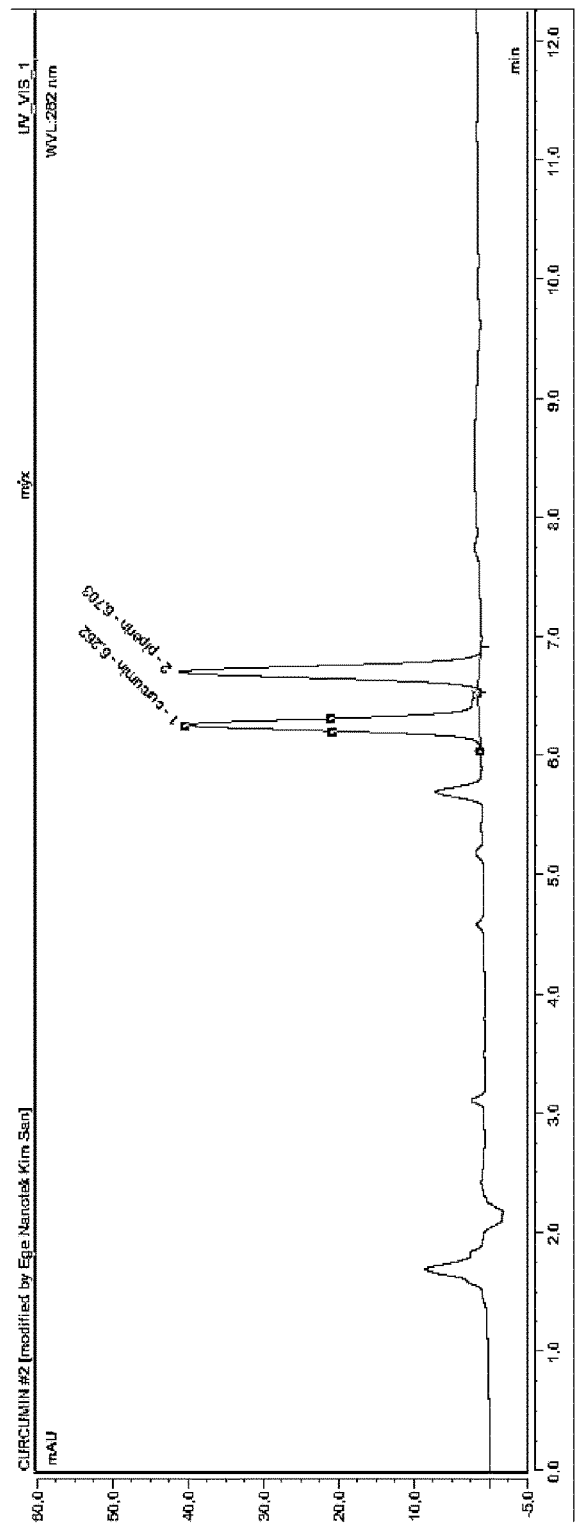

FIG. 3: is the view of the peaks of curcumin and piperine found in the extracts.

Figure 4:
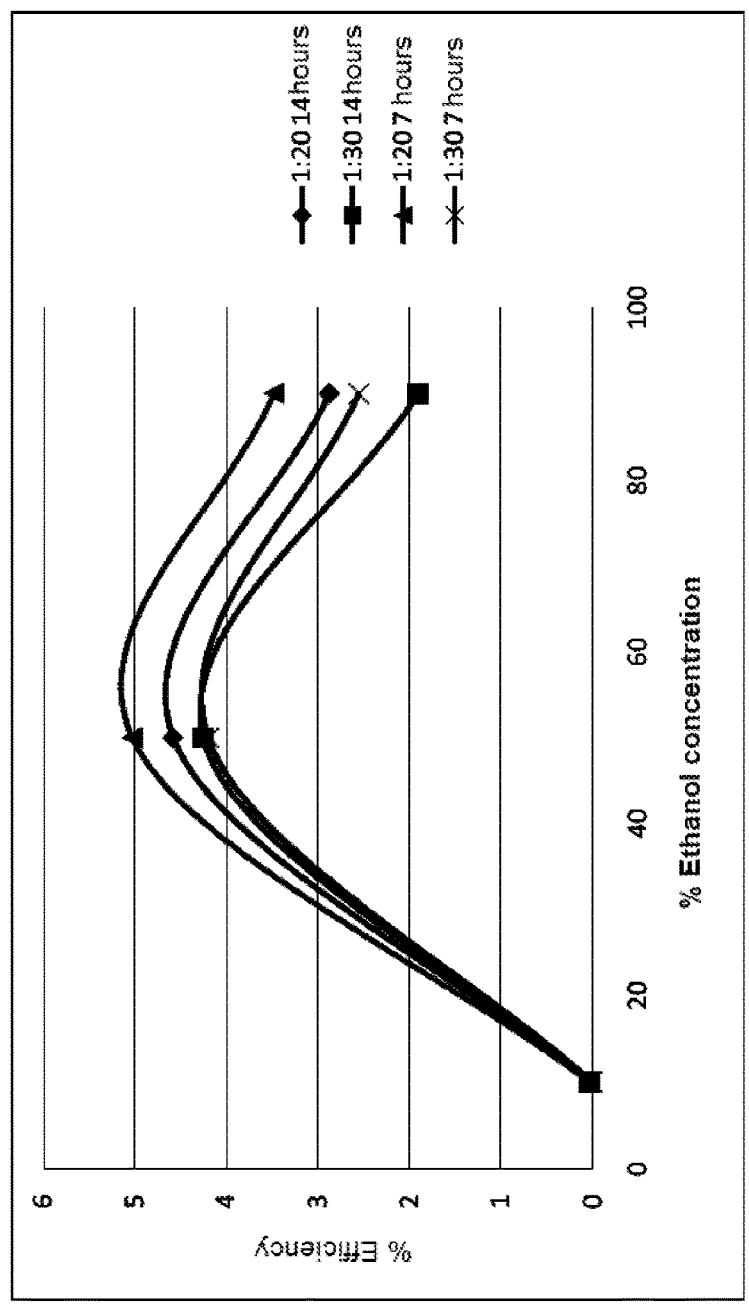

FIG. 4: is the view of the graph showing the change in the extraction efficiency of curcumin in accordance with the parameters.

Figure 5:
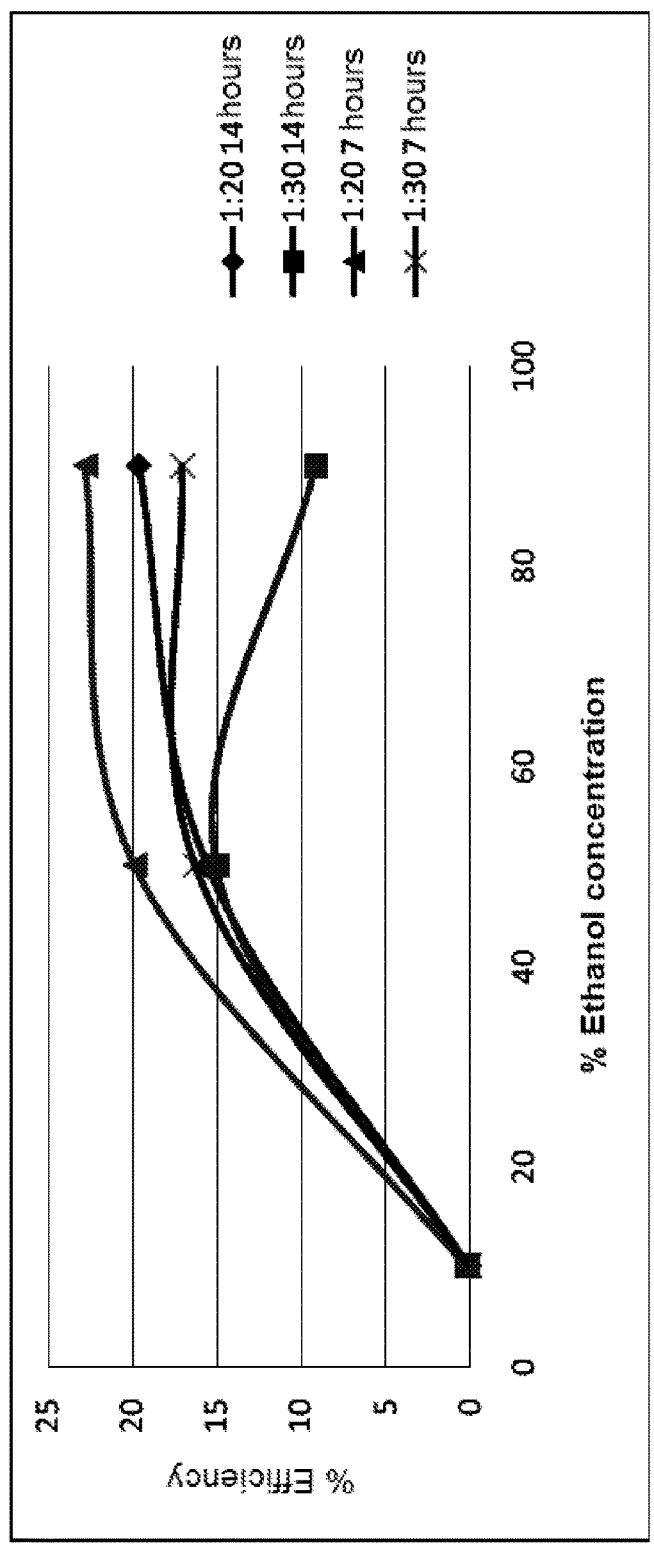

FIG. 5: is the view of the graph showing the change in the extraction efficiency of piperine in accordance with the parameters.

Figure 6:
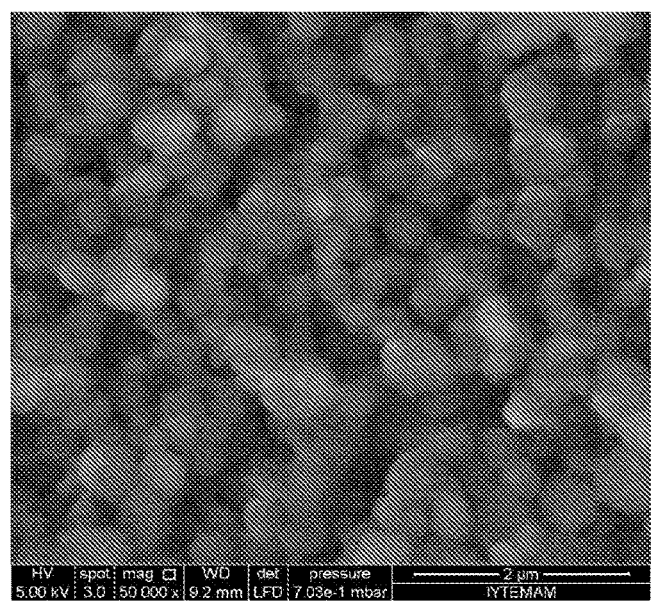

FIG. 6: shows the scanned electron microscope views of nano/micro particles.

Figure 7:
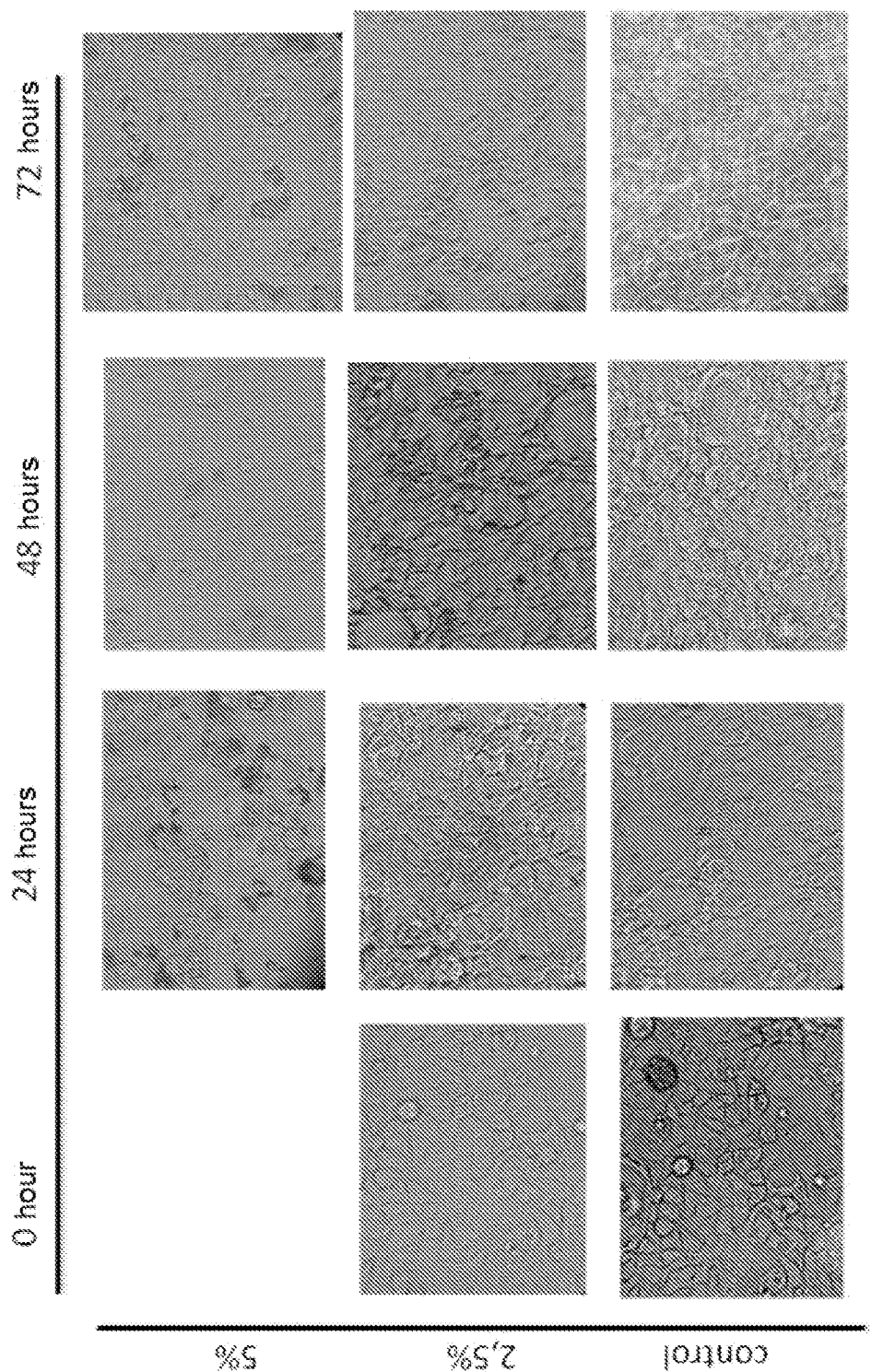

FIG. 7: shows the cell line views following application of different doses of nanoformulations for Caco-2 colon cancer cell line.

Drawings do not have to be scaled and details not necessary for understanding the present invention may be neglected. Moreover, components which are at least widely equal or which have at least widely equal functions are shown with the same number.

REFERENCE NUMBERS

1. Double-layered nano/micro particle
2. Outer shell layer
3. Core layer
4. Collector
5. Syringe
6. Micro and nanospheres
7. Power source
8. Coating container
9. Solution containing piperine
10. Liquid product

DETAILED DESCRIPTION OF THE INVENTION

In this detailed description, the preferred embodiments of the development of curcumin and piperine loaded double-layered biopolymer based nano delivery systems by using electrospray/coating method, which is the subject of the invention, will only be disclosed for better understanding of the subject, and will not form any limiting effect.

The invention relates to encapsulation of the liquid extracts of *curcuma* comprising the active agent curcumin and/or its derivatives and black pepper comprising the active agent piperine into double-layered nanoparticles (1) manufactured using the natural polymers zein and chitosan and/or its derivatives via electrospray/coating method. In this way, the cellular ingestion efficiency of nanoparticles (1) is improved. Moreover, the natural active agent curcumin can be delivered to a certain targeted tissue and it can reach the targeted site while maintaining its stability, and by means of its piperine content, cellular ingestion of curcumin is made easier and thus its bioavailability and efficiency can be improved.

Prepared nanoparticles (1) are used in food supplemental formulations with varying ratios by dispersion into solutions (liquid product) (10) formed of plantal glycerine and water mixture.

Zein, also known as maize protein, is a biopolymer that can be used in food and drug delivery systems among other natural polymers with its biocompatibility, biodegradability, and low inflammation risk. Natural delivery systems have replaced synthetic delivery systems due to their characteristics such as biocompatibility, biodegradability, low cost, and various chemical modifications and processability. Proteins such as collagen, gelatine, elastin, albumin, and silk fibroin are commonly used for this purpose (Wenk et al., 2008). Protein structures have recently been used in bioengineering applications as coating materials for continuous drug release, microspheres for encapsulation in drug delivery systems, and biomaterials such as films in controlled drug release (Bayraktar et al., 2005). In this context, in order to enable the natural compounds show effective biological activities while maintaining their stability, these compounds are required to be encapsulated by natural carriers found in the biopolymer structure.

By means of comprising both hydrophobic and hydrophilic aminoacids, it provides versatile processability option (Sanchez-Garcia et al., 2010; Parris et al., 2005; Torres-Giner et al., 2010). Low water retention values, high thermal resistance, physical and chemical barrier-forming characteristics enables its use as an edible coating on foods and drugs (Torres-Giner et al., 2010). For instance, it is known that zein is used for the purpose of providing stability and controlled release for oil-based food supplements frequently used in the industry such as flax oil. Products encapsulated in zein, which maintain their bioactivity for long periods and which become biodegradable in time, are frequently encountered in the food sector (Quispe-Condori et al., 2011). In another study, fiber formation is made by zein and its change and release profile is examined by means of adding a polyphenol structure to this fibered structure (Li & Kakuda, 2009).

As a natural biopolymer, chitosan is obtained by deacetylation of chitosan chitin, which is a polysaccharide formed of glucosamine and N-acetyl-glucosamine copolymers. The chitin polymer essentially has the structure of: poly-b-(1,4)-2-acetamide-2-deoxy-b-D glucopiranose, and also comprises very low amounts of 2-amino-2-deoxy-b-glucopiranose monomer. On the other hand, chitosan is a D-deacetylated derivative of chitin having the structure of: 2-2-deoxy-b-D-glucopiranose.

Chitosan is used in various industries including especially food, cosmetics, medicine, pharmaceutics, and textile. It is commonly used as synthetic skin and blood vessels, controlled drug release systems, contact lens, band aid, surgical suture and gauze, tumour inhibitor, antifungal, antibacterial, and hemostatic biomaterials (4). Moreover, encapsulation of natural antioxidants into micro- and nano-particle-formed structures using chitosan is studied in the literature (5).

Development of electrospray/coating method has provided the encapsulation method, which is a more economical and practical process providing quicker results. Since it is a different approach than the stringent conditions (such as high temperature application) in other conventional encapsulation applications, it is regarded as a more advantageous technique for studies comprising bioactive agents due to its biocompatibility.

The encapsulation method according to the invention is electrospray/coating method. Said method; has a different approach than the stringent conditions (such as high temperature application) in other conventional encapsulation applications of the prior art, and thus it is a more advantageous technique for protein-based studies and bioactive compounds due to its biocompatibility. Moreover, while the electrospray method enables maintaining the stability of materials during encapsulation, it is also more successful than the other methods in terms of a delivery system.

With the electrospray/coating method, an outer shell layer (2) comprising black pepper extract with the active agent piperine is formed on the core layer (3) comprising curcuma extract via coating method, and double-layered nano/micro particles (1) are prepared. Hydrophobicities of the active agents to be encapsulated within the double-layered nanoparticles (1) are taken into account. The zein found within the hydrophobic structure that would form the core layer (3) is combined with curcumin and piperine content is added into the outer shell layer (2) formed of chitosan and its derivatives. Use of the natural biopolymers zein and chitosan in formation of nanoparticles is also important to prevent formation of inflammation in interbody uses, due to the biocompatibility and low cytotoxic activities of these substances.

In a preferred embodiment of the invention, the most efficient way of obtaining curcumin from curcuma is by solid-liquid extraction method within 70% ethyl alcohol. As can also be seen from the studies of the prior art, curcumin can be efficiently encapsulated within the hydrophobic structures due to hydrophobic interactions and can protect their stabilities in these kind of structures for longer periods. At the same time, it has rheological characteristics enabling change of sphere size via electrospray method.

Chitosan and its derivatives are used for the purpose of forming a layer around the internal core part (3) and encapsulating piperine within this layer, and then rapidly release the encapsulated piperine onto the application site. Said chitosan derivative is preferably carboxymethyl chitosan. By means of using chitosan and carboxymethyl chitosan in different molecular weights (low, middle, and high molecular weights), piperine can be stably encapsulated on the chitosan layer (2) found around the zein core part (3).

Curcuminoids comprise curcumin and/or its derivatives. Said derivatives are desmethoxycurcumin and Bis-desmethoxycurcumin.

In FIG. 1, the schematic view of the process of obtaining the double-layered nano/micro particles (1) comprising standardized curcuma and black pepper extracts via electrospray/coating method is given. In said system; a collector (4), a syringe (5), micro and nanospheres (6), a power source (7), a coating container (8), a solution containing piperine (9) and a liquid product (10) are used.

Production Method:
Optimization of curcuma and black pepper extraction operation and extract characterization:

Optimum extraction conditions are determined for both plant materials considering the antioxidant and antimicrobial characteristics.

Procedures Used:
grinding curcuma and black pepper plant materials into small particle size,
exposure to a certain time period of extraction via ethanol-water mixture,
filtration for separating solids and liquids,
removal of the ethanol part of the liquid extract obtained in the form of aqueous ethanol by means of vacuum treatment under low temperature conditions,
afterwards, keeping the water-phase liquid extract that does not contain residual ethanol in settling tanks at low temperature conditions, and
obtaining, in water-phase, curcuma and black pepper liquid extracts rich in polyphenolic compounds at optimum conditions.

Performing encapsulation and its characterization

It comprises formation of a chitosan shell part (2) comprising black pepper extract with the active agent piperine via coating method on the core part (3) formed of zein comprising curcuma extract via electrospray/coating method, and preparing double-layered particles (1). Said particles (1) can be nano- or micro-sized particles.

Nano/micro formulation:
Afterwards, prepared particles (1) are dispersed into solutions formed of plantal glycerine and water mixture in varying ratios and used in food supplemental formulations.

Assay Results:
Extraction Studies:

Extraction studies are made according to various parameters for maximum extraction of curcumin and piperine found within curcuma and black pepper. These parameters are found in the below given table.

TABLE 1

Extraction Parameters

| Variable | Level 1 | Level 2 | Level 3 |
|---|---|---|---|
| Ethanol Ratio (%) | 10 | 50 | 90 |
| Extraction Time (Hour) | 7 | 14 | 21 |
| Solid-Liquid Ratio | 1:10 | 1:20 | 1:30 |

As a result of the studies, curcumin and piperine are determined at the same time via HPLC analysis.

TABLE 2

| HPLC specifications | |
|---|---|
| Colon type | C18 3 μm 120 Å 4.6 × 150 mm |
| Colon Temperature | 33° C. |
| Flow rate | 0.8 ml/min. |
| Mobile Phase | % 0.1 Phosphoric Acid Aqueous Solution, Acetonitrile 45:55 (v/v) |
| Detector Wavelength | 262 nm |
| Method | Isocratic |

In FIG. 2a, the peak for 97% purity curcumin and its derivatives (desmethoxycurcumin and Bis-desmethoxycurcumin); and in FIG. 2b, the peak for piperine is shown. FIG. 3 shows the peaks of the extract active agents curcumin and piperine and the peaks of the active agents simultaneously.

Results of Extraction Studies:
Efficiency calculations are made by making use of extraction operations and the results are shown on the graph. The results for curcumin are shown in FIG. 4. As shown in the graph of FIG. 4, the efficiency has increased with the increase of the solid-liquid ratio. Besides, it can be seen that the maximum efficiency can be obtained at 60-70% ethanol rates.

In FIG. 5, the graph of change in piperine efficiency according to the parameters is given. In contrast to curcumin, in piperine, the maximum concentration is achieved as a result of studies made in higher alcohol concentrations.

Performing Encapsulation and its Characterization:

*Curcuma* extract is encapsulated by applying the below given parametric study via electrospray method using the mixture prepared by mixing zein dissolved in 70% (v/v) ethanol with the extract at predetermined concentrations.

In chitosan; first of all, chitosan (carboxymethyl chitosan) is dissolved and mixed in water comprising 1-2% of acetic acid for at least 16 hours. Coating liquid is obtained by means of mixing the aqueous solution comprising 1-5% chitosan with the black pepper liquid extract obtained as a result of extraction operation considering the viscosity of the solution mixture obtained. This solution comprising piperine with appropriate viscosity is placed within the coating container of the electrospray operation and the curcumin formed as a result of electrospray is used in formation of the outer shell layer by means of coating the outer parts of the encapsulated zein micro/nano particles.

Besides said variables, the distance between the syringe and the collector (4), the flow rate of the syringe (5), and other variables are kept constant. Morphologies of the encapsulated samples are examined under scanning electron microscope (SEM).

The piperine concentration in the chitosan solution found within the coating container of the mechanism in FIG. 1 is kept constant.

| Variable | Level 1 | Level 2 | Level 3 |
|---|---|---|---|
| Voltage | 10 kV | 12 kV | 15 kV |
| Extract:zein mixture | 1:10 | 1:20 | 1:50 |

Cytotoxicity and Antitumor Test for the Prepared Nano Formulation a. Cell Culture Within the framework of this study, MCF7 and NIH3T3 (Mouse embryonic fibroblast) cell lines are used. Cell lines are prepared in incubators comprising 5% $CO_2$, at 37° C., at concentrations suitable for cell lines, and cultured in DMEM or RPMI broth comprising penicillin and streptomycin with addition of 10% FBS.

b. Determination of cytotoxic activity via MTT (tetrazolium (3-{4,5-dimethylthiazol-2-yl}-2,5-diphenyl tetrazolium bromide) method Sterilized solution comprising the extract and the nano/microcapsule is seeded in 96-well plates prepared in suitable growth medium, and they are treated onto adsorbed cancer cell lines and NIH3T3 healthy mouse fibroblast cells. The cytotoxic response of the samples incubated at certain periods is determined with tetrazolium (3-{4,5-dimethylthiazol-2-yl}-2,5-diphenyl tetrazolium bromide-based colorimetric method. Following incubation with the material extract for predetermined time periods, MTT solution is added into each well and the absorbance values obtained after 4 hours of incubation are converted into vitality percent. In this way, while the toxic effect on healthy cells is examined, at the same time, the presence of growth inhibiting characteristics of the tumour cell is also examined for the cancer cell line.

After the results are obtained, the encapsulated extract is also exposed to vitality and antitumor assays, and the contribution of the microsphere formation in the study to the biological activity is determined.

In FIG. 6, preparations are made such that the voltage would be 15 kV, flow rate 0.65 ml/hour, lycopene 1:20 by weight, and Etoh 70%. Average diameter is 0.13 micron. Smooth circular structures are observed.

As shown in FIG. 6, the optimum conditions for the use of samples are found as 15 kV current, 0.65 ml/hour flow rate, 1:20 rate of *curcuma* extract, and 70% alcohol rate.

After said nanoformulation is reported as a result of an in vitro study made on growth inhibiting effect comprising preparation under 5 different dilutions in 3 different cancer cell lines. Following proliferation of prostate cancer cell line (PC3), breast cancer cell line (MCF7), and colon cancer cell line (Caco), cytotoxicity test is applied and the change in the vitality of cancer cells treated with the extract for 24, 48, and 72 hours via MTT assay is measured by optical methods. The results obtained are analyzed and given below.

The prepared nanoformulation may have cytotoxic effect with samples of 10% concentrations on breast cancer. However, the solution comprising the extract in free form in the same concentration with the nanoformulation does not show a cytotoxic effect. The free-form extract can only show cytotoxic effect at 25% concentration.

Significant findings were obtained on colon cancer. High rate of reduction in cell vitality was obtained in vitro with 5% concentration nanoformulation.

The effects on the prostate cancer was the same with the other two cancer line findings such that 50% death in cancer cell vitality was obtained with 10% concentration of nanoformulation.

With the nanoformulation, the bioavailability within the extract was increased by 60%. Nanoformulation was especially effective on colon cancer cell line.

In FIG. 7, cell line microscope views following application of varying doses of nanoformulation for Caco-2 colon cancer cell line are shown. In said Figure, while the cells that are used as control maintain their numbers and morphologies for 72 hours; the number of cells, or in other words, vitality is reduced especially after $72^{nd}$ hour, since 2.5% part of the cell growth medium is formed of nanoformulation.

This situation leads to reduction in cell viability in a shorter time such as 48 hours and in a more severe manner when 5% of the cell growth medium is formed of nanoformulation. And this shows that the formulations we have prepared effectively cause reduction in the viability of cancer cells.

REFERENCES

1) Sangeeta K. Cheema, Andrea S. Gobin, Robyn Rhea, Gabriel Lopez-Berestein, Robert A. Newman, Anshu B. Mathur, "Silk fibroin mediated delivery of liposomal emodin to breast cancer cells" International Journal of Pharmaceutics Volume 341, Issues 1-2, 16 Aug. 2007, Pages 221-229.
2) Curcumin-Piperinee/Curcumin-Quercetin/Curcumin-Silibinin dual drug-loaded nanoparticulate combination therapy: A novel approach to target and treat multidrug-resistant cancers (C. Moorthi, K. Kathiresan)—January 2013.
3) Preparation and characterization of curcumin-piperine dual drug loaded nanoparticles (C. Moorthi, K. Kathiresan, R. Manavalan, K. Kathiresan)—November—2012.
4) Montazer, M., Afjeh, G., 2007, Simultaneous X-Linking and Antimicrobial Finishing of Cotton Fabric, Journal of Applied Polymer Science, Vol. 103, p. 178-185.
5) R. Harris, E. Lecumberri, I. Mateos-Aparicio, M. Mengíbar, A. Heras, Chitosan nanoparticles and microspheres for the encapsulation of natural antioxidants extracted from *Ilex paraguariensis*, Carbohydrate Polymers, Volume 84, Issue 2, 1 Mar. 2011, Pages 803-806.

The invention claimed is:

1. A method for producing a double-layered nano-sized particle comprising:
   encapsulating an active agent curcumin or desmethoxycurcumin or bis-desmethoxycurcumin in a core layer formed of zein protein by electrospraying;
   encapsulating an active agent piperine in an outer shell layer formed of chitosan or carboxymethyl chitosan by electrospraying; and
   coating the outer shell layer over the core layer.

2. The method of claim 1, further comprising:
   obtaining the curcumin or desmethoxycurcumin or bis-desmethoxycurcumin from a extract of *curcuma*.

3. The method of claim 1, further comprising:
   obtaining the piperine from an extract of black pepper.

* * * * *